United States Patent
Lee et al.

(10) Patent No.: US 10,098,616 B2
(45) Date of Patent: Oct. 16, 2018

(54) INSERTABLE PROBE FOR DIAGNOSIS OF LESIONAL TISSUE IN REAL TIME AND METHOD OF MANUFACTURING ELECTRODE THEREOF

(71) Applicant: GWANGJU INSTITUTE OF SCIENCE AND TECHNOLOGY, Gwangju (KR)

(72) Inventors: Jong Hyun Lee, Gwangju (KR); Giseok Kang, Gwangju (KR); Jae-Cheon Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 438 days.

(21) Appl. No.: 14/096,764

(22) Filed: Dec. 4, 2013

(65) Prior Publication Data

US 2014/0163414 A1 Jun. 12, 2014

(30) Foreign Application Priority Data

Dec. 6, 2012 (KR) .......................... 10-2012-0141040

(51) Int. Cl.
*A61B 10/02* (2006.01)
*A61B 5/053* (2006.01)
*A61B 5/00* (2006.01)

(52) U.S. Cl.
CPC ........ *A61B 10/0283* (2013.01); *A61B 5/0538* (2013.01); *A61B 5/6851* (2013.01)

(58) Field of Classification Search
CPC ...... A61B 10/0283; A61B 5/0538; G02B 6/00
See application file for complete search history.

(56) References Cited

U.S. PATENT DOCUMENTS

| | | | |
|---|---|---|---|
| 5,476,100 A * | 12/1995 | Galel ................ | A61M 25/0155 600/466 |
| 2003/0018281 A1* | 1/2003 | Huitema ............ | A61B 10/0275 600/567 |
| 2003/0083724 A1* | 5/2003 | Jog ...................... | A61N 1/0536 607/122 |
| 2004/0249268 A1* | 12/2004 | Da Silva ............. | A61B 5/0059 600/424 |

(Continued)

FOREIGN PATENT DOCUMENTS

| | | |
|---|---|---|
| JP | 2007-519474 A | 7/2007 |
| JP | 2011036521 A | 2/2011 |
| KR | 101148187 B1 | 5/2012 |

OTHER PUBLICATIONS

Korean Notice of Allowance dated Aug. 29, 2014.
Korean Office Action dated Jan. 29, 2014.

*Primary Examiner* — Sean Dougherty
*Assistant Examiner* — Patrick Fernandes
(74) *Attorney, Agent, or Firm* — Hauptman Ham, LLP

(57) ABSTRACT

Disclosed herein is an insertable probe for diagnosis of lesional tissue in real time. The insertable probe includes a guide needle inserted into the human body and having a hollow shape of a predetermined length, a storage connected to the guide needle, a tissue collection portion collecting a predetermined amount of tissue in the human body and moving the collected tissue to the storage through the guide needle, and an inspection unit inspecting the tissue stored in the storage. A method of manufacturing an electrode using the same is also disclosed.

12 Claims, 17 Drawing Sheets

(56) References Cited

U.S. PATENT DOCUMENTS

| | | | |
|---|---|---|---|
| 2008/0132805 A1* | 6/2008 | Heywang-Koebrunner | ................ A61B 10/0275 600/566 |
| 2008/0221480 A1* | 9/2008 | Hibner | ............... A61B 10/0275 600/566 |
| 2009/0112118 A1* | 4/2009 | Quick, Jr. | .......... A61B 10/0275 600/564 |
| 2010/0286507 A1* | 11/2010 | Paassilta | ................ A61B 5/053 600/424 |
| 2011/0028837 A1* | 2/2011 | Byrd | ................... A61B 5/0071 600/433 |
| 2011/0105948 A1* | 5/2011 | Halter | ................... A61B 5/053 600/567 |

* cited by examiner

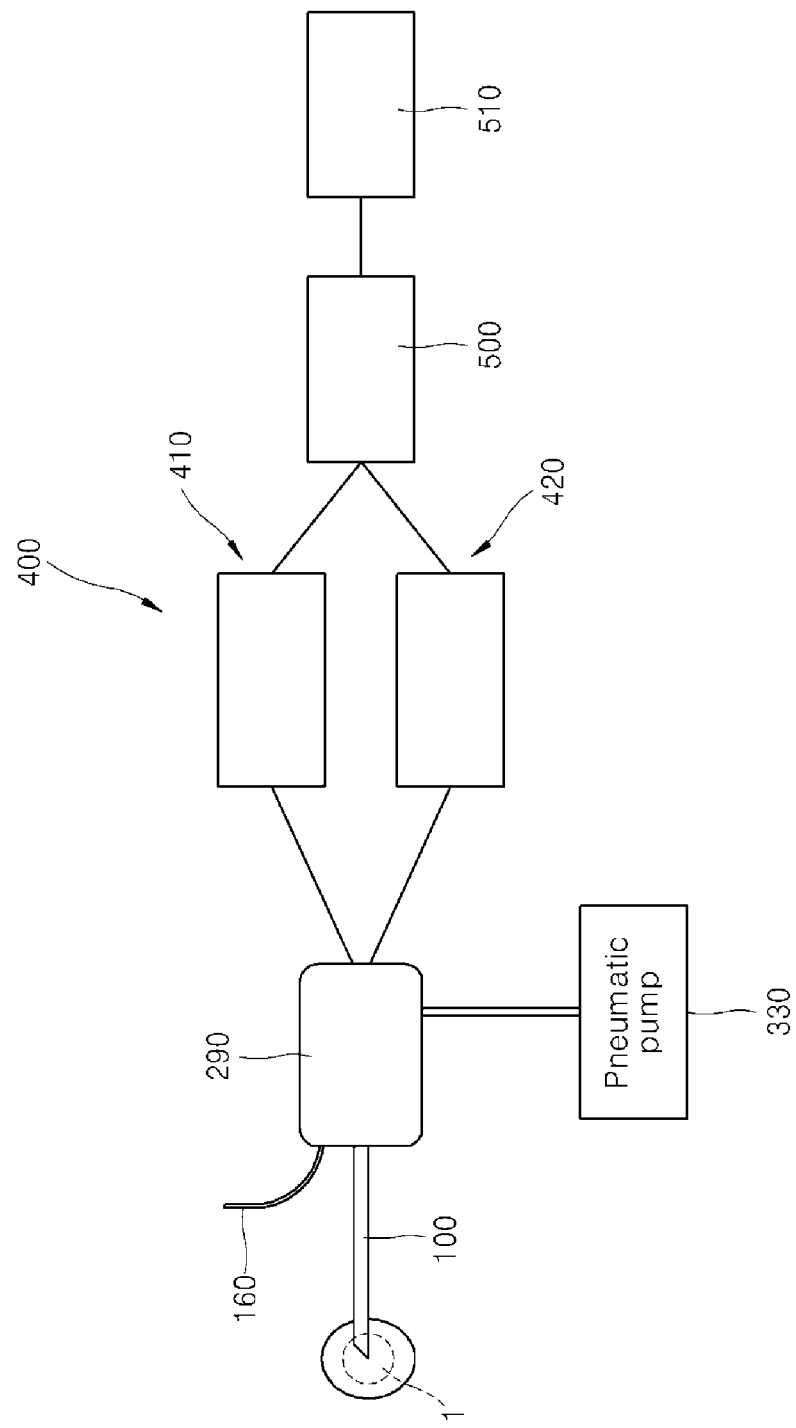
[Fig. 1]

[Fig. 2]
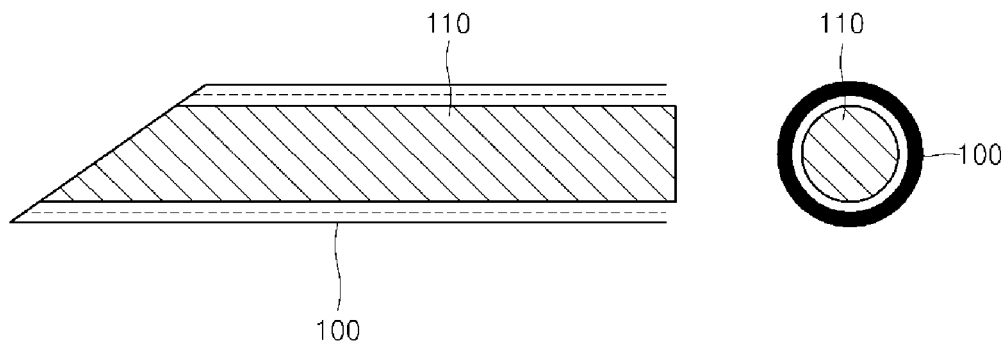
[Fig. 3a]
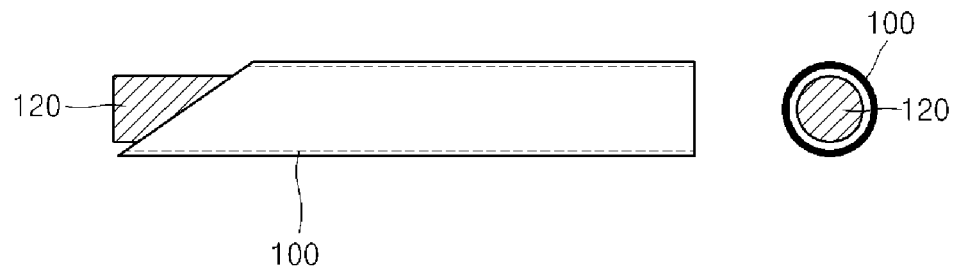
[Fig. 3b]
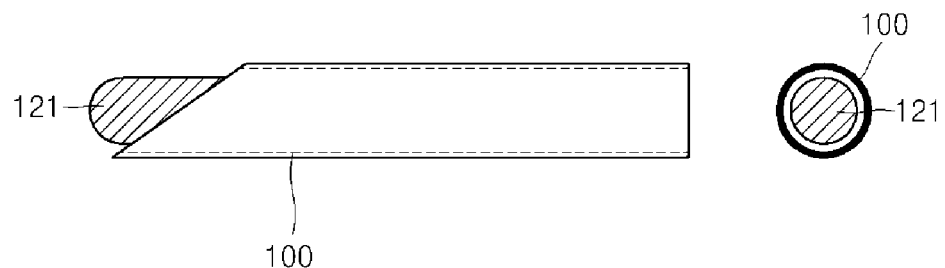

[Fig. 3c]
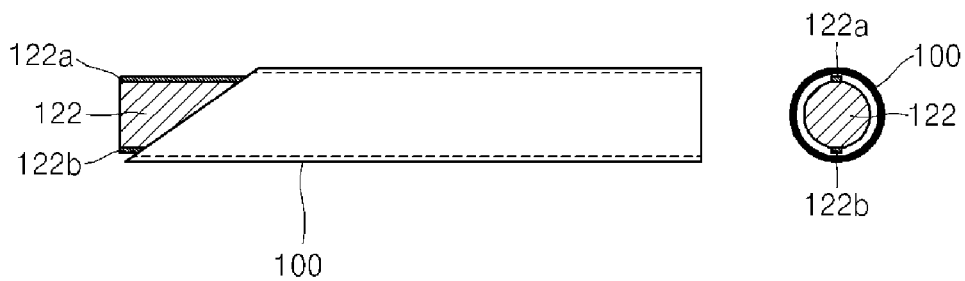
[Fig. 4a]
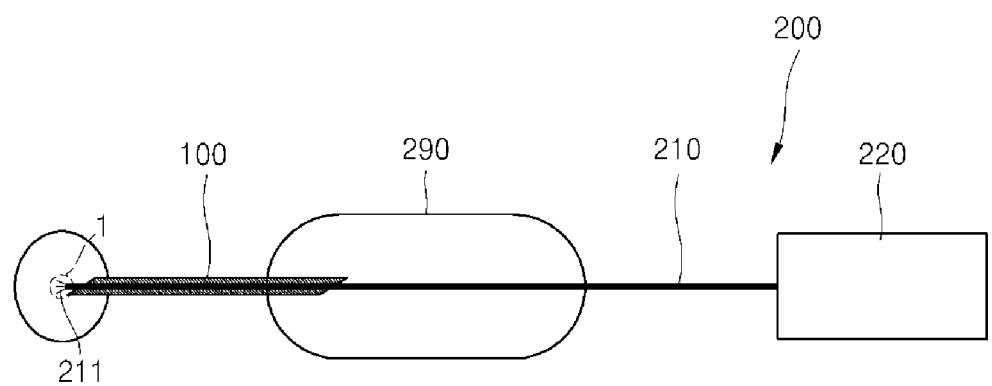
[Fig. 4b]
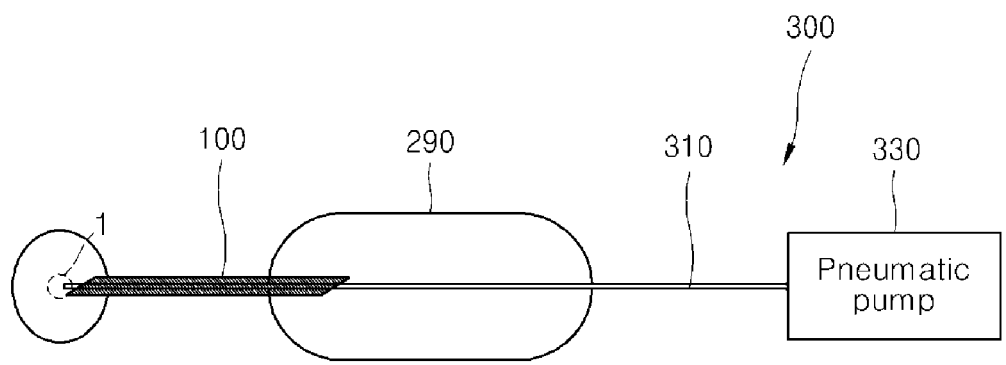

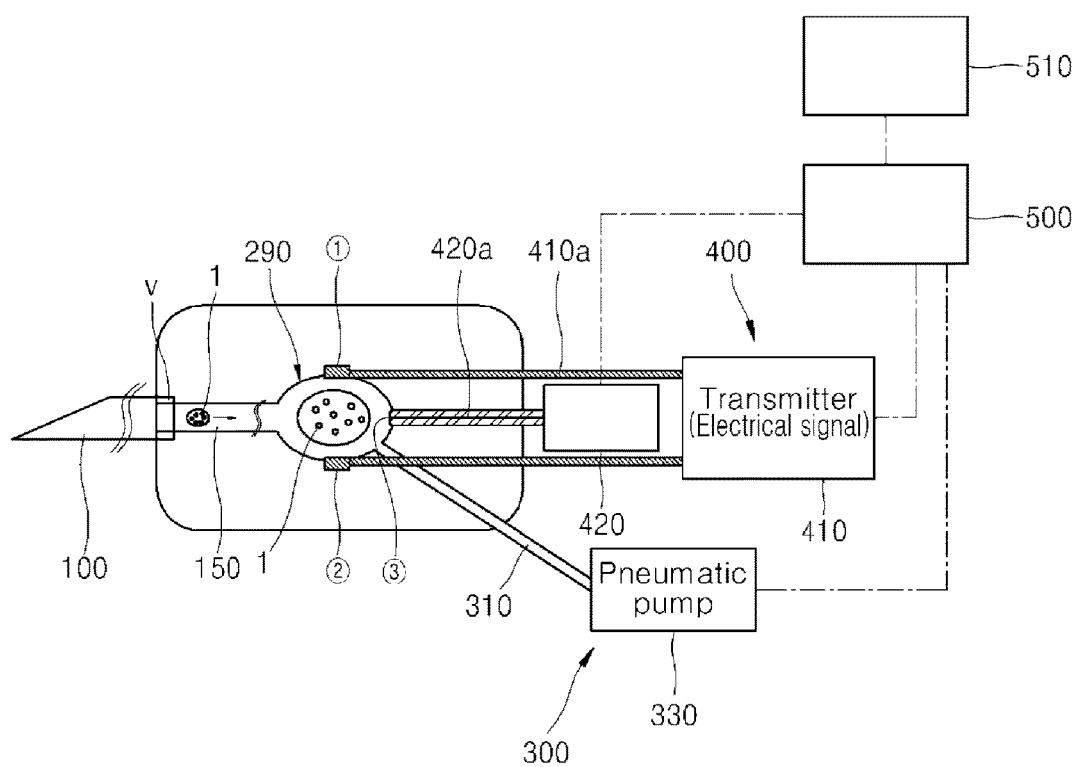
[Fig. 5a]

[Fig. 5b]
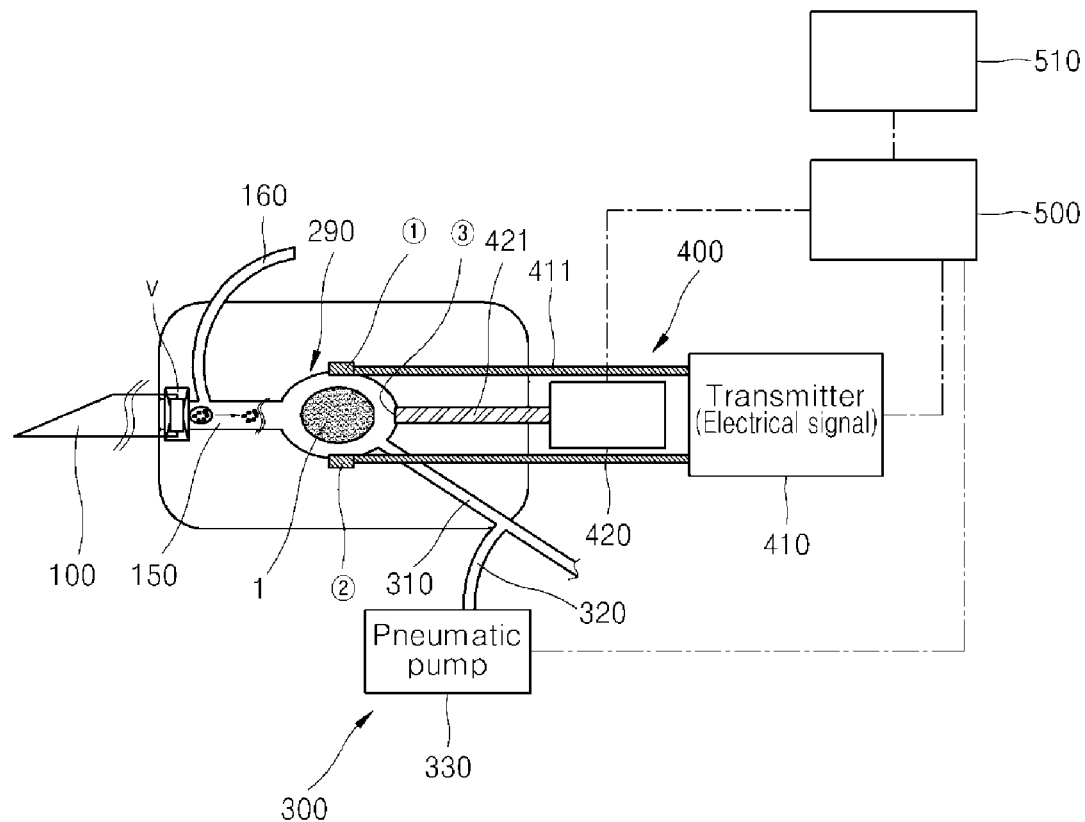
[Fig. 6a]
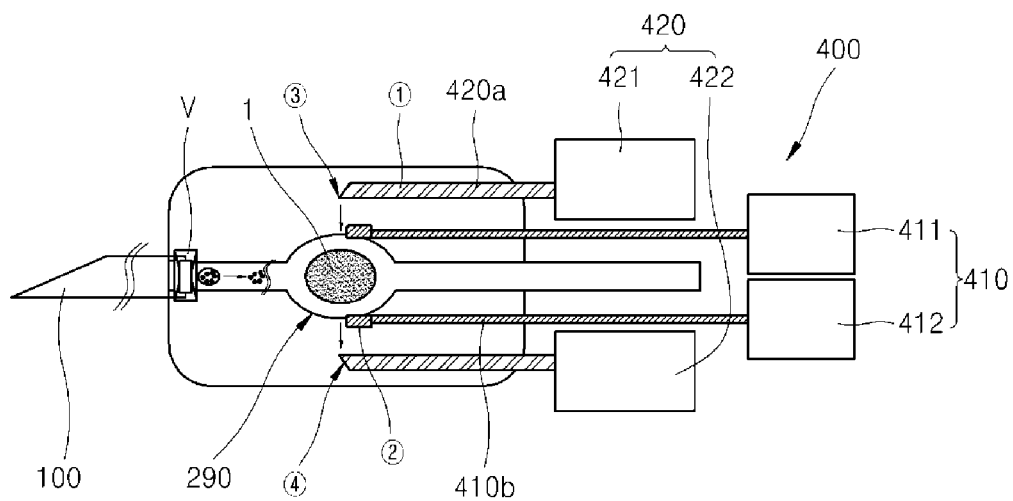

[Fig. 6b]
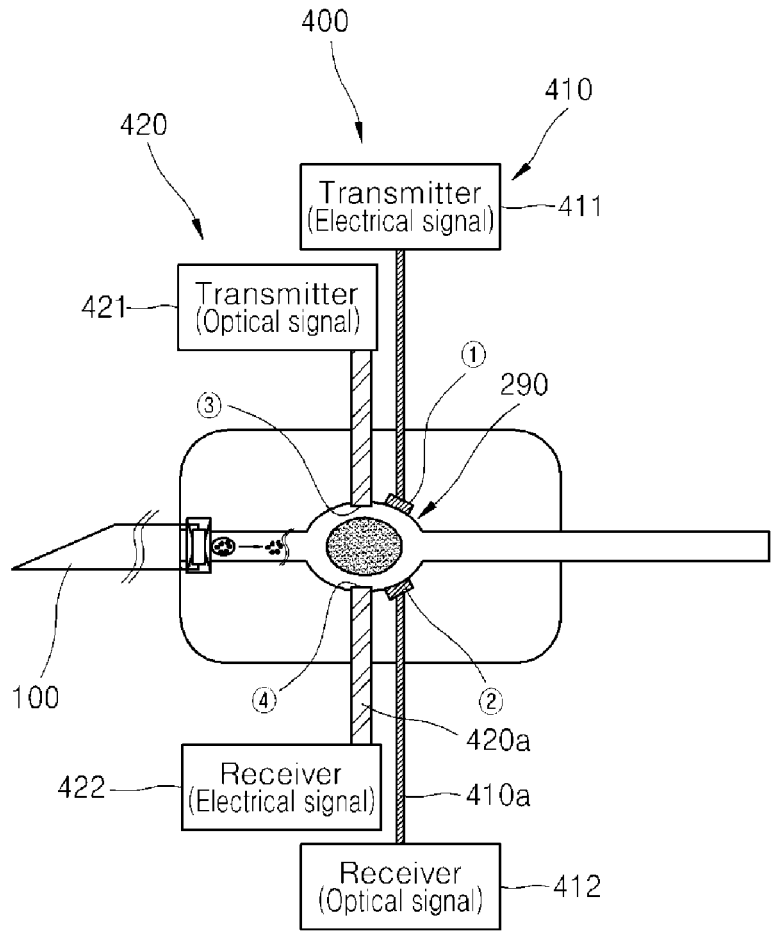
[Fig. 7a]
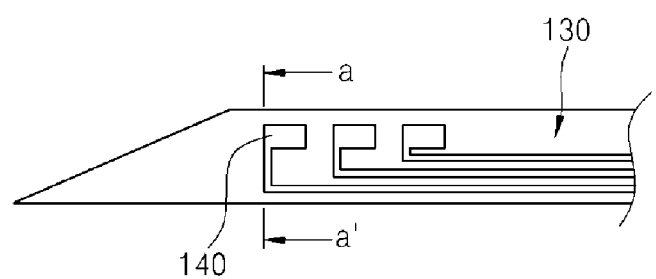

[Fig. 7b]
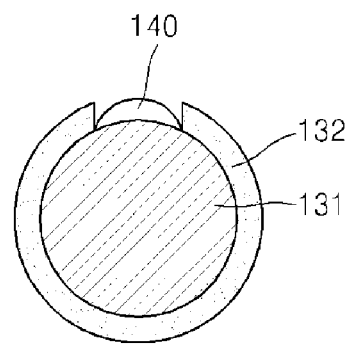
[Fig. 7c]
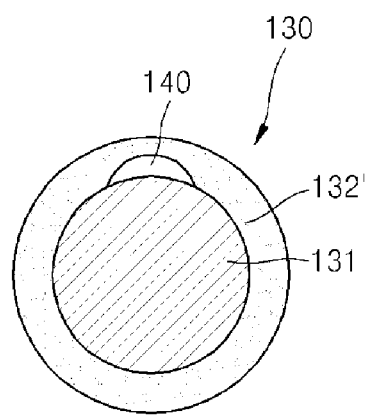

[Fig. 8a]
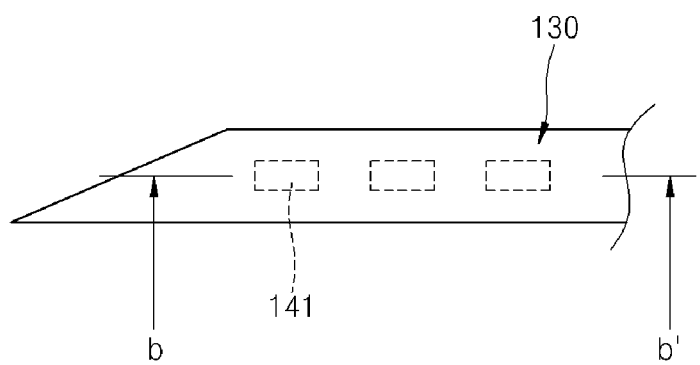
[Fig. 8b]
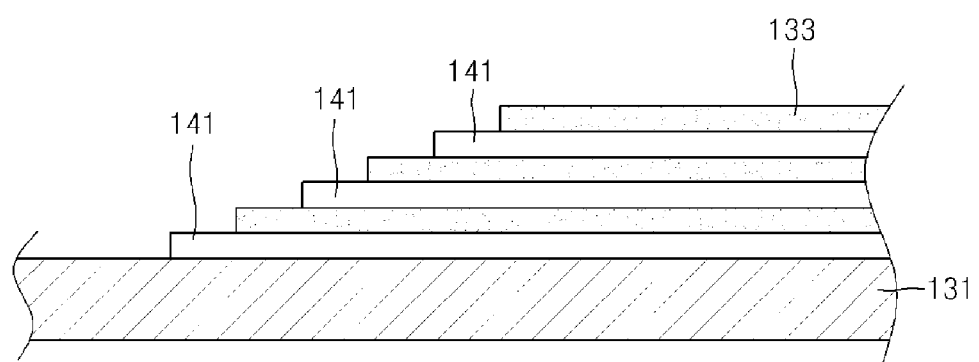

[Fig. 8c]
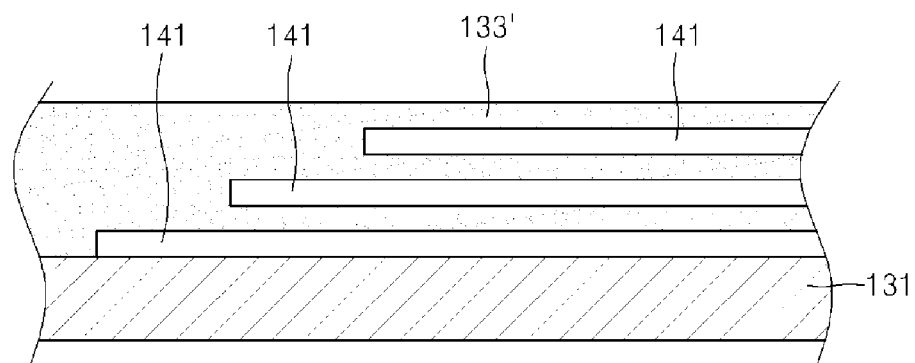
[Fig. 9a]
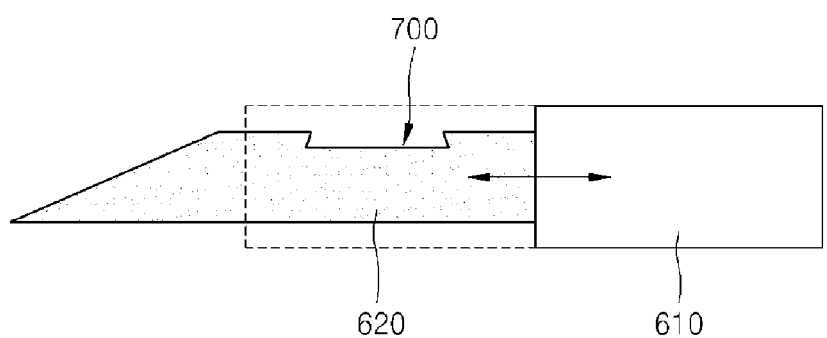

[Fig. 9b]
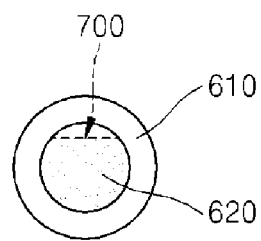
[Fig. 10a]
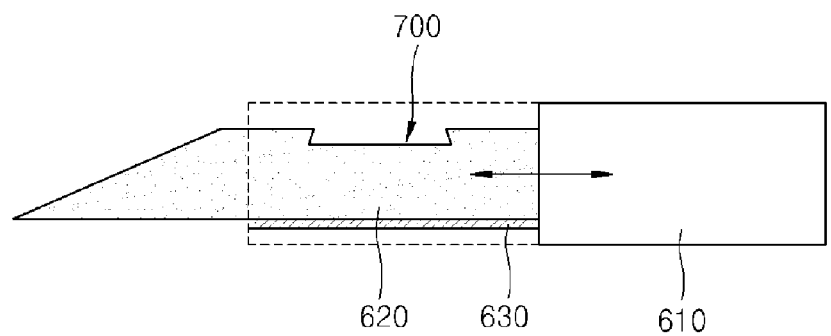
[Fig. 10b]
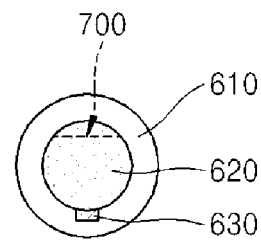

[Fig. 11a]
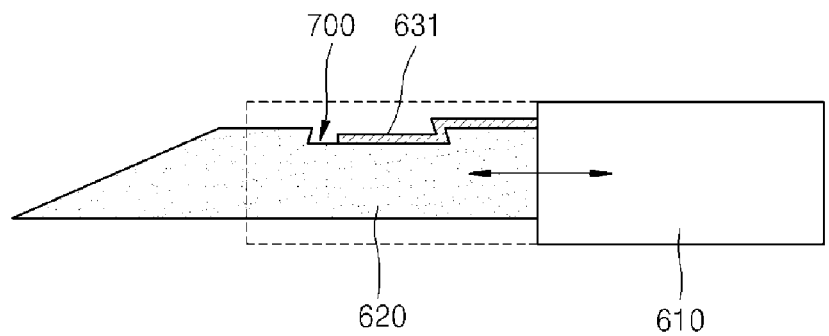
[Fig. 11b]
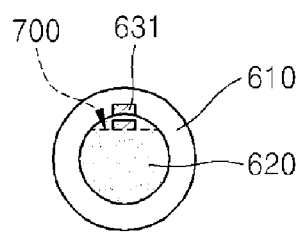
[Fig. 12a]
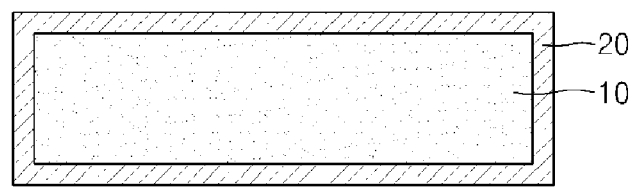

[Fig. 12b]
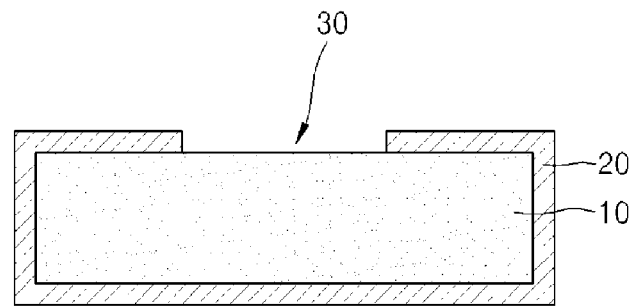
[Fig. 12c]
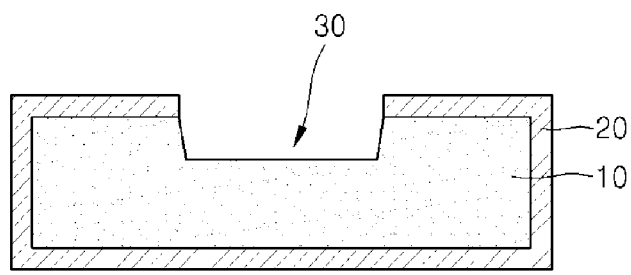
[Fig. 12d]
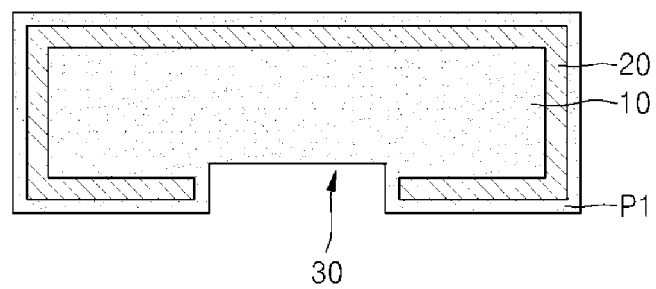

[Fig. 12e]
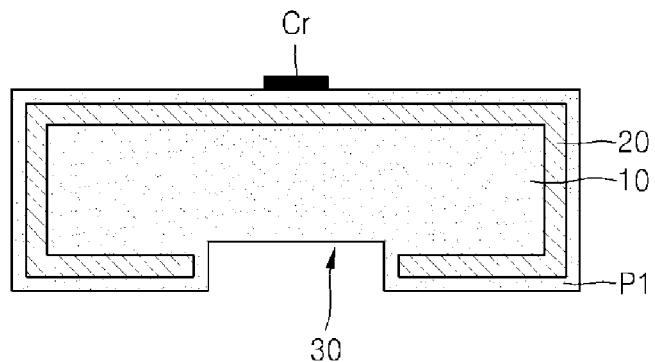
[Fig. 12f]
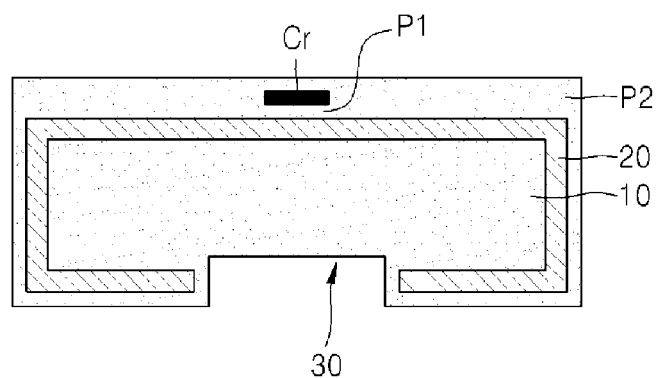
[Fig. 12g]
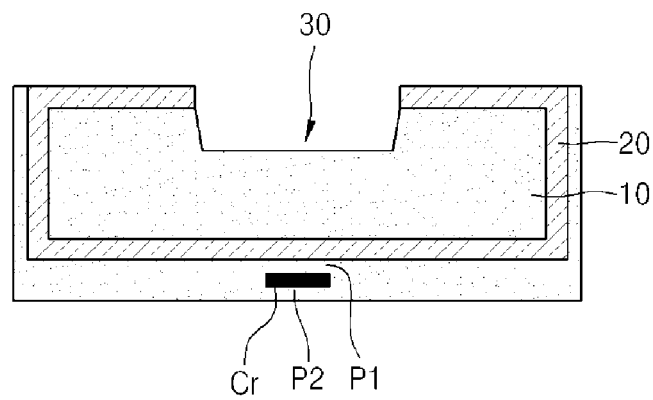

[Fig. 12h]
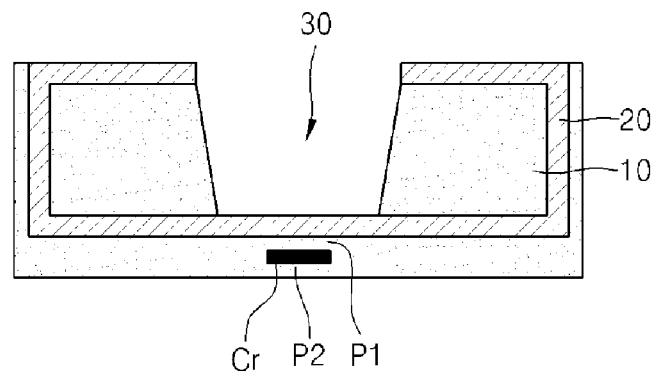
[Fig. 12i]
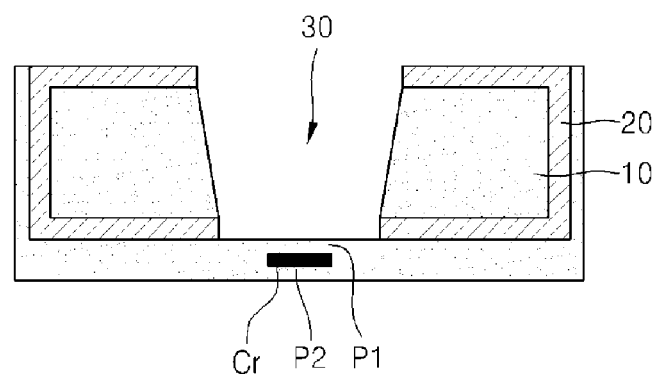
[Fig. 13a]
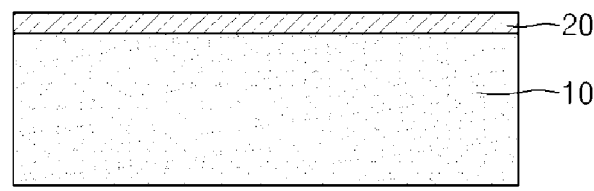

[Fig. 13b]
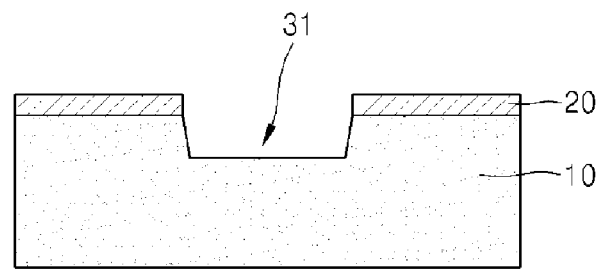
[Fig. 13c]
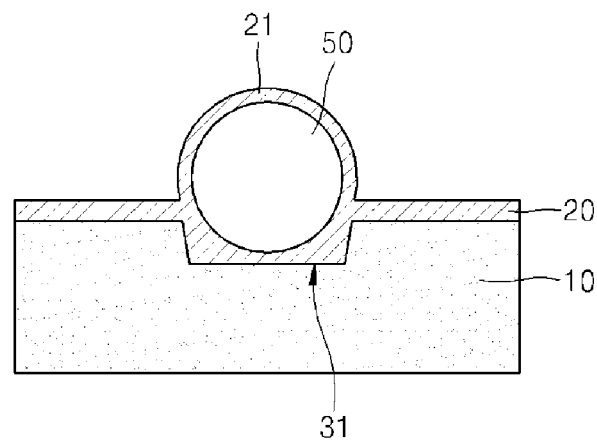

[Fig. 14a]
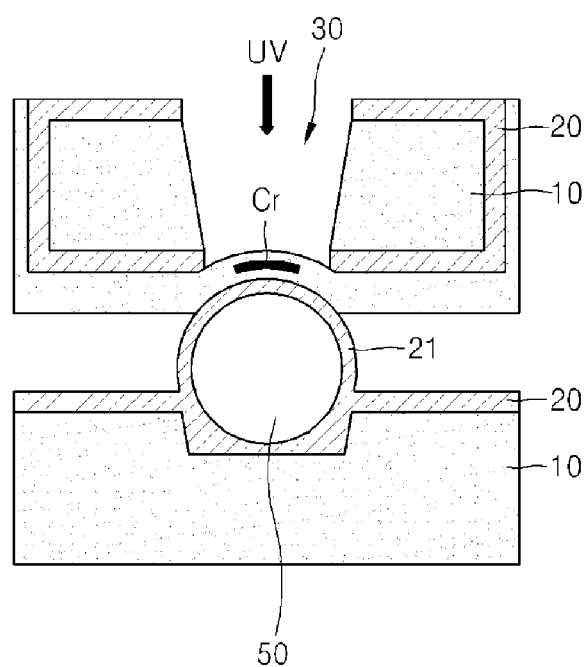
[Fig. 14b]
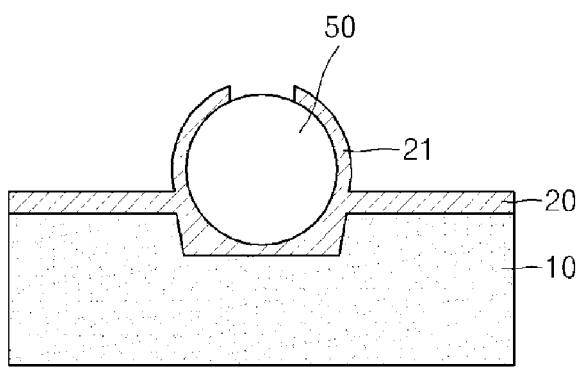

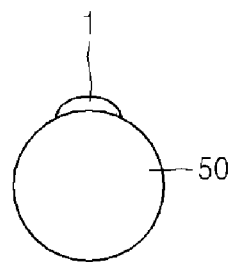
[Fig. 14c]

INSERTABLE PROBE FOR DIAGNOSIS OF LESIONAL TISSUE IN REAL TIME AND METHOD OF MANUFACTURING ELECTRODE THEREOF

CROSS-REFERENCE TO RELATED APPLICATION

This application claims priority to Korean Patent Application No. 10-2012-0141040 filed on 6 Dec. 2012, and all the benefits accruing therefrom under 35 U.S.C. § 119, the contents of which is incorporated by reference in its entirety.

BACKGROUND

1. Technical Field

The present invention relates an insertable probe, and more particularly, to an insertable probe for diagnosis of lesional tissue in real time, which can collect lesional tissue in the human body and inspect the collected lesional tissue in real time, and a method of manufacturing an electrode thereof.

2. Description of the Related Art

In general, general methods for diagnosis of a lesion of the human body include imaging diagnosis using X-rays, ultrasound, and endoscopes.

Although various information (size, location, progress, and the like) of a lesion through imaging diagnosis may help a doctor make a diagnosis, tissue of a portion that is doubted to be lesional tissue must be collected and inspected for clear diagnosis of the lesional tissue. That is, a biopsy must be performed on the tissue.

In order to collect a tissue sample, a hollow needle is used to suction a considerable amount of lesional tissue, or surgery is performed to expose the lesional tissue.

In biopsy, a series of complex procedures for physical or chemical processing after collection of lesional tissue takes several hours to several days, causing a possibility of variation in actual characteristics of the tissue in the course of the procedures.

In determination of biopsy results by pathologists, diagnosis reliability can be increased when quantitative diagnosis data is added at an initial stage of a disease.

When a biopsy is performed on a lesion that is small or located at a dangerous position, various problems can occur. For example, in the case of the thyroid gland, since it is difficult to find an accurate location of a needle even with the help of an external imaging apparatus (ultrasound waves), a success rate of biopsy is low and the number of biopsies is limited due to the small size of the thyroid.

BRIEF SUMMARY

An aspect of the present invention is to provide an insertion probe for diagnosis of lesional tissue in real time, which can collect lesional tissue at a predetermined depth within the human body, and can electrically and optically diagnose and inspect the collected lesional tissue in real time, and a method of manufacturing the same.

In accordance with one aspect of the present invention, an insertable probe for diagnosis of lesional tissue in real time includes: a guide needle inserted into the human body and having a hollow shape of a predetermined length; a storage connected to the guide needle; a tissue collection portion collecting a predetermined amount of tissue in the human body and moving the collected tissue to the storage through the guide needle; and an inspection unit inspecting the tissue stored in the storage.

The guide needle may be formed of a metal; a region of the guide needle to be inserted into the human body except for one end of the guide needle may be coated with an insulating material; an anti-clogging needle having an outer diameter smaller than an inner diameter of the guide needle may be disposed within the guide needle; and the one end of the guide needle and the anti-clogging needle may be different electrodes to acquire an electric signal regarding the tissue.

The guide needle may be formed of a metal; a region of the guide needle to be inserted into the human body except for one end of the guide needle may be coated with an insulating material; an anti-clogging needle having an outer diameter smaller than an inner diameter of the guide needle may be disposed within the guide needle; the guide needle or the anti-clogging needle may have a plurality of different electrodes; the electrodes may be disposed on a surface of the anti-clogging needle to be exposed outside; and the electrodes may have a predetermined minimum linewidth to acquire an electric signal regarding the tissue.

The electrodes may be formed at the same height from a surface of the guide needle or the anti-clogging needle, or at different heights from the surface thereof; the electrodes may be separated from each other; a portion or the entirety of surfaces of the electrodes may be coated with an insulating material; an electric signal may be applied to the electrodes and measured simultaneously or individually; and an electric signal regarding the tissue may be acquired.

An inner cylinder having an outer diameter smaller than an inner diameter of the guide needle may be disposed within the guide needle and may be formed of an optical fiber to acquire an optical signal regarding the tissue.

An inner cylinder having an outer diameter smaller than an inner diameter of the guide needle may be disposed within the guide needle and may be provided on a circumference thereof with different electrodes to acquire an electric signal regarding the tissue.

The guide needle or the inner cylinder may be provided with a plurality of different electrodes, and the electrodes may have a predetermined minimum linewidth to acquire an electric signal regarding the tissue.

The electrodes may be formed at the same height from a surface of the guide needle or the anti-clogging needle, or at different heights from the surface thereof; the electrodes may be separated from each other; a portion or the entirety of surfaces of the electrodes may be coated with an insulating material; an electric signal may be applied to the electrodes and measured simultaneously or individually, and an electric signal regarding the tissue may be acquired.

The tissue collection portion may include: a tissue moving line connecting an interior space of the guide needle to the storage; a wire disposed within the guide needle and the tissue moving line and provided at one end thereof with a tissue collecting member to collect a predetermined amount of tissue in the human body; and a drive unit connected to an opposite end of the wire to pull or release the wire such that the tissue in the human body is placed in the storage.

The tissue collection portion may include: a tissue moving line connecting an interior space of the guide needle to the storage; and a pneumatic pump connected to the storage and suctioning the tissue in the human body through the tissue moving line to store the suctioned tissue in the storage.

The tissue collection portion may include a tissue moving line connecting a tissue collecting tool to the storage, and may suction the tissue in the human body through the tissue moving line to store the suctioned tissue in the storage.

The probe further may include an actuator, and the actuator may vary a cross-section of a channel securing the tissue stored in the storage using a predetermined pneumatic pressure.

A medicine introduction line through which a predetermined amount of medicine for disrupting the tissue into individual cells may be further connected to the tissue moving line.

The medicine introduction line on the tissue moving line may be provided at a front end thereof with a reverse-flow prevention valve to prevent reverse flow of the tissue stored in the storage.

The inspection unit may include an electric signal inspector and an optical signal inspector.

The electric signal inspector may include: an electric signal transmitter disposed at a first location of a circumference of the storage and transmitting an electric signal to the tissue stored in the storage; and an electric signal receiver disposed at a second location of the circumference of the storage and receiving an electric signal including electric impedance and electric current of the tissue; and the optical signal inspector may include: an electric signal transmitter disposed at a third location of the circumference of the storage and transmitting an optical signal to the tissue stored in the storage; and an optical signal receiver disposed at a fourth location of the circumference of the storage and receiving an optical signal including an index of refraction at the tissue and an intensity of light.

In accordance with another aspect of the present invention, an insertable probe for diagnosis of lesional tissue in real time includes: a hollow outer needle; an inner needle inserted into a hollow portion of the outer needle to be horizontally moved in a longitudinal direction of the outer needle and having a sharp distal end; and a tissue collection portion formed in the inner needle to collect a predetermined amount of tissue.

The tissue collection portion may be formed in a recess shape having a predetermined depth on a circumference of the inner needle.

The probe may have one or a plurality of electrodes, and the electrodes may be disposed on an outer circumference of the inner needle.

The electrodes may be disposed in close contact with the outer circumference and a surface of the tissue collection portion.

In accordance with another aspect of the present invention, a method of manufacturing an electrode includes: depositing a polymer (for example, parylene) to form a photomask having different electrode patterns; securing an anti-clogging needle or an inner cylinder, followed by coating a photoresist onto the anti-clogging needle or the inner cylinder; and forming an electrode in a curved structure using the anti-clogging needle or the inner cylinder coated with the photoresist.

The depositing a polymer may include: depositing a nitride on a silicon substrate; forming a pattern of a membrane section of the photomask on the nitride; etching the silicon substrate to a predetermined depth in a thickness direction of the silicon substrate; depositing first parylene on the nitride and the silicon substrate; depositing chromium on the first parylene and forming patterns of different electrodes; depositing second parylene on the chromium; etching the first parylene and the second parylene in the membrane section; etching the silicon substrate such that all of a remaining depth of the silicon substrate is etched; and removing the nitride.

The securing an anti-clogging needle or an inner cylinder may include: depositing a nitride on a silicon substrate and forming a securing mold pattern of the anti-clogging needle or the inner cylinder on the nitride; etching the silicon substrate to a predetermined depth in a thickness direction of the silicon substrate to form a securing mold of the anti-clogging needle or the inner cylinder; placing the anti-clogging needle or the inner cylinder in the securing mold to secure the anti-clogging needle or the inner cylinder; and coating the photoresist onto the anti-clogging needle or the inner cylinder.

The forming an electrode may include: aligning the anti-clogging needle or the inner cylinder secured to the securing mold and the photomask such that the anti-clogging needle or the inner cylinder and the photomask contact each other; projecting UV light to the photoresist through the photomask to form patterns of different electrodes at desired locations of the curved surface of the anti-clogging needle or the inner cylinder; and depositing a metal and removing the photoresist to form the electrode.

According to embodiments the invention, lesional tissue placed at a predetermined depth of the human body may be collected and the collected lesional tissue may be electrically and optically diagnosed and inspected in real time.

According to the embodiments of the invention, a diameter of the guide needle is set to below 5 mm, whereby destruction of tissue in the human body may be minimized through the guide needle and pain of a patient may be minimized.

According to the embodiments of the invention, since electrical and optical inspection information may be obtained in real time by inserting the guide needle at a portion that is doubted to be lesional tissue of a patient, a time consumed in tissue diagnosis may be shortened and accuracy of diagnosis may be increased.

According to the embodiments of the invention, since inspection information may be monitored and stored in real time, diagnosis by a surgical operator may be assisted, and the inspection information may be compared and analyzed later.

BRIEF DESCRIPTION OF THE DRAWINGS

The above and other aspects, features, and advantages of the present invention will become apparent from the detailed description of the following embodiments in conjunction with the accompanying drawings, in which:

FIG. 1 is a schematic view of an insertable probe for diagnosis of lesional tissue in real time according to the present invention;

FIG. 2 is a view of a guide needle according to the present invention, in which an anti-clogging needle is disposed;

FIG. 3a is a view of a guide needle according to the present invention, in which an inner cylinder is disposed;

FIG. 3b is a view of a guide needle according to the present invention, in which another inner cylinder is disposed;

FIG. 3c is a view of a guide needle according to the present invention, in which another inner cylinder is disposed;

FIG. 4a is a view of a probe including a tissue collection portion according to the present invention;

FIG. 4b is a view of a probe employing another tissue collection portion according to the present invention;

FIG. 5a is a view of an insertable probe for diagnosis of lesional tissue in real time according to one embodiment of the present invention;

FIG. 5b is a view of the insertable probe for diagnosis of lesional tissue in real time according to the present invention, which includes a medicine introduction line;

FIG. 6a is a view of the insertable probe for diagnosis of lesional tissue in real time according the present invention, which includes an inspection unit;

FIG. 6b is a view of the insertable probe for diagnosis of lesional tissue in real time according to the present invention, which includes another inspection unit;

FIG. 7a is a sectional view of an insertable probe for diagnosis of lesional tissue in real time according to another embodiment of the present invention;

FIG. 7b is a sectional view taken along line a-a' of FIG. 7a;

FIG. 7c is a view of an insertable probe for diagnosis of lesional tissue in real time according to a further embodiment of the present invention;

FIG. 8a is a view of an insertable probe for diagnosis of lesional tissue in real time according to yet another embodiment of the present invention;

FIG. 8b is a sectional view taken along line b-b' of FIG. 8a;

FIG. 8c is a view of an insertable probe for diagnosis of lesional tissue in real time according to yet another embodiment of the present invention;

FIG. 9a is a sectional view of another embodiment of the tissue collection portion according to the present invention;

FIG. 9b is a longitudinal sectional view of another embodiment of the tissue collection portion according to the present invention;

FIG. 10a is a sectional view of one example in which an electrode is disposed on a bottom surface of an anti-clogging needle of FIG. 9a;

FIG. 10b is a longitudinal sectional view of the example in which the electrode is disposed on the bottom surface of the anti-clogging needle of FIG. 10a;

FIG. 11a is a sectional view of one example in which an electrode is disposed on a tissue collection portion of FIG. 9a;

FIG. 11b is a longitudinal sectional view of the example in which the electrode is disposed in the tissue collection portion of FIG. 9a; and FIGS. 12a to 14c are sectional views showing a method of manufacturing an electrode according to the present invention

DETAILED DESCRIPTION

Embodiments of the present invention will now be described with reference to the accompanying drawings.

First, an insertable probe for diagnosis of lesional tissue in real time according to one embodiment of the present invention will be described.

FIG. 1 shows a schematic configuration of an insertable probe for diagnosis of lesional tissue in real time according to one embodiment of the present invention.

Referring to FIG. 1, the insertable probe for diagnosis of lesional tissue in real time according to the embodiment includes a guide needle 100, a tissue collection portion 200, a storage 290, and an inspection unit 400.

The tissue collection portion 200 of FIG. 1 will be described below.

FIG. 2 shows a guide needle according to the present invention, in which an anti-clogging needle is disposed.

Referring to FIG. 2, the guide needle 100 has a hollow shape and has a predetermined length.

The guide needle 100 has a predetermined inner diameter. The guide needle 100 has a tapered end(s).

One end of the guide needle 100 corresponds to a portion substantially introduced into the human body by a predetermined depth.

The guide needle 100 is formed of a metal. Here, an area of one end of the guide needle 100 except for a predetermined portion may be coated with an electrically insulating material to form an insulating coating layer having a predetermined thickness. The insulating coating may be formed of a polymer material.

Thus, the one end of the guide needle 100 is formed of a metal.

An anti-clogging needle 110 formed of a metal is inserted into the guide needle 100.

The anti-clogging needle 110 has a smaller diameter than an inner diameter of the guide needle 100 by a predetermined size.

Thus, as shown in FIG. 2, a space is formed between an outer circumference of the anti-clogging needle 110 and an inner circumference of the guide needle 100.

Here, when one end of the guide needle 100 is inserted into the human body, the anti-clogging needle 110 serves to prevent tissue from being introduced into the guide needle 100.

The one end of the guide needle 100 having no insulation coating and the anti-clogging needle 110 act as different electrodes.

That is, when the one end of the guide needle 100 reaches lesional tissue in the human body, the different electrodes act as one electrical sensor, through which an electric signal of the lesional tissue can be acquired to obtain characteristics thereof. The electric signal may include electric impedance and electric current at the lesional tissue Thus, a controller 500 of FIG. 1 may perform a biopsy on lesional tissue in real time according to a level of the electric signal.

FIG. 3a is a view of a guide needle according to the present invention, in which an inner cylinder is disposed, and FIG. 3b is a view of a guide needle according to the present invention, in which another inner cylinder is disposed.

Referring to FIG. 3a, an inner cylinder 120 is inserted into the guide needle 100 according to the present invention.

The inner cylinder 120 has a circular rod shape and has an outer diameter smaller than an inner diameter of the guide needle 100.

Thus, a space is formed between an inner circumference of the guide needle 100 and an outer circumference of the inner cylinder 120.

As shown in FIG. 3a, a side sectional shape of one end of the inner cylinder 120 may have a right angle.

As shown in FIG. 3b, a side sectional shape of one end of the inner cylinder 121 may have a convex shape in a longitudinal direction of the inner cylinder 121.

The inner cylinders 120, 121 may be formed of optical fibers.

Here, since the one end of the inner cylinder 121 shown in FIG. 3b has a convex shape, the inner cylinder may easily induce focusing of light.

That is, when one end of the guide needle 100 reaches lesional tissue in the human body, the inner cylinders 120, 121 may act as one optical sensor through which an optical signal of the lesional tissue can be acquired to obtain characteristics.

Thus, the controller 500 of FIG. 1 may perform a biopsy on lesional tissue in real time according to a level of the optical signal.

FIG. 3c is a view of a guide needle according to the present invention, in which another inner cylinder is disposed.

In another example, referring to FIG. 3c, the inner cylinder 122 may have a shape, as shown in FIG. 3a.

Here, different electrodes 122a, 122b are formed on an outer surface of the inner cylinder 122 in the longitudinal direction thereof.

Thus, when one end of the guide needle 100 reaches lesional tissue in the human body, the different electrodes 122a, 122b may act as one electrical sensor through which an electric signal of the lesional tissue can be acquired to obtain characteristics. The electric signal may include electric impedance and electric current of the lesional tissue.

Thus, the controller 500 of FIG. 1 may perform a biopsy on lesional tissue in real time according to a level of the electric signal.

Next, the tissue collection portion according to the invention will be described.

FIG. 4a shows a probe including a tissue collection portion according to the present invention.

Referring to FIG. 4a, a tissue collection portion 200 according to one embodiment of the invention may include a tissue moving line 150, a wire 210, and a drive unit 220.

The tissue moving line 150 is a line connecting the guide needle 100 to the storage 290, and forms a passage through which tissue moves.

The wire 150 may be disposed within the guide needle 100 and the tissue moving line 150.

The wire 150 is provided at one thereof with a tissue collecting member 211. The tissue collecting member 211 may have a hook or a filter net, which can collect lesional tissue 1 of the human body.

The wire 150 may be wound by the drive unit 220. That is, the drive unit 220 may pull or release the wire 150.

Thus, when the guide needle 100 is inserted into the human body by a predetermined depth, the tissue collecting member 211 disposed at one end of the wire 210 may collect a predetermined amount of lesional tissue 1 of the human body.

Subsequently, the drive unit 220 winds the wire 210, thereby allowing the lesional tissue 1 collected by the tissue collecting member 211 to be stored in the storage 290.

FIG. 4b is a view of a probe employing another tissue collection portion according to the present invention.

Referring to FIG. 4b, a tissue collection portion 300 according to another embodiment may include a tissue moving line 150, a pneumatic line 310, and a pneumatic pump 330.

The tissue moving line 150 may be substantially the same as the tissue moving line, as shown in FIG. 4a.

The pneumatic pump 330 includes a pneumatic line 310 connected to the tissue moving line 150. The pneumatic pump 330 may form a compulsory suction force in the guide needle 100 and the tissue moving line 150.

Thus, when the guide needle 100 is inserted into the human body by a predetermined depth, the pneumatic pump 330 forms a compulsory suction force or a pumping force.

The tissue 1 in the human body may be moved to the storage 290 through the guide needle 100 and the tissue moving line 150 by the compulsory suction force.

As described above, according to the present invention, a predetermined amount of tissue 1 in the human body may be collected using the tissue collecting member 211 or a pneumatic pressure.

FIG. 5a is a view of an insertable probe for diagnosis of lesional tissue in real time according to one embodiment of the present invention.

Referring to FIG. 5a, configuration and operation of the probe having an inspection unit 400 according to the present invention will be described.

The guide needle 100 according to the present invention is connected to a tissue moving line.

The tissue moving line 150 is connected to the storage 290. The storage 290 provides a space in which a predetermined amount of tissue 1 is temporarily stored.

The inspection unit 400 according to the present invention includes an electric signal inspector 410 and an optical signal inspector 420.

The electric signal inspector 410 includes an electric signal transmitter 411 disposed at a first location ① on a circumference of the storage 290 and transmitting an electric signal to the tissue 1 stored in the storage 290, and an electric signal receiver 412 disposed at a second location ② on the circumference of the storage 290 and receiving an electric signal including electric impedance and electric current of the tissue 1.

The electric signal transmitter 411 and the electric signal receiver 412 may be connected to each other by an electric signal line 410a.

The optical signal inspector 420 includes an electric signal transmitter 421 disposed at a third location ③ on the circumference of the storage 290 and transmitting an optical signal to the tissue 1 stored in the storage 290, and an optical signal receiver 422 disposed at a fourth location ④ on the circumference of the storage 290 and receiving an optical signal including an index of refraction at the tissue 1 and an intensity of light.

The optical signal transmitter 421 and the optical signal receiver 422 may be connected to each other by an optical fiber.

The pneumatic line 310 may be connected to the storage 290. The pneumatic pump 330 may be disposed on the pneumatic line 310 to discharge the tissue 1 to the outside along the pneumatic line 310 after inspection.

Here, the first and second locations and may be set at locations of the storage 290 facing each other, and the third location may be set in the storage 290 between the first and second locations and.

The probe may further include an actuator (not shown).

The actuator may vary a cross-section of a channel that secures tissue stored in the storage 290 using a predetermined pneumatic pressure.

In this structure, the guide needle 100 may be inserted into the human body by a predetermined depth. The lesional tissue 1 may be placed at an insertion location.

The pneumatic pump 330 receives a control signal through the controller 500 that is not shown, and forms a compulsory suction force in the pneumatic line 310.

A predetermined amount of lesional tissue 1 in the human body is introduced into the guide needle 100 by the compulsory suction force, and is moved to and stored in the storage 290 along the tissue moving line 150.

Then, operation of the pneumatic pump 220 may be stopped by the controller 500.

Here, although not shown, the storage 290 may further include a pressure sensor (not shown) that can detect whether tissue is stored therein.

The pressure sensor measures a pressure instantaneously varying when the tissue 1 is stored in the storage 290, and transmits the measured pressure to the controller 500.

When receiving the pressure measured by the pressure sensor, the controller 500 may stop operation of the pneumatic pump 330.

Here, the configuration of stopping operation of the pneumatic pump 330 in response to a signal indicating that the tissue 1 is stored in the storage 290 is not limited thereto.

Thus, when the tissue 1 is stored in the storage 290, the controller 500 performs electrical and optical inspection on the stored tissue 1 using the inspection unit 400.

First, the electric signal transmitter 411 transmits an electric signal to the tissue 1 stored in the storage 290 at the first location ① on the circumference of the storage 290.

The electric signal receiver 412 receives an electric signal including electric impedance and electric current of the tissue 1 at the second location ② on the circumference of the storage 290.

The received electric signal may be transmitted to the controller 500.

The controller 500 may compare the received electric signal with a level of a preset reference electric signal, and may inspect and determine a biopsy of the lesional tissue 1 in real time.

Further, the optical signal transmitter 421 transmits an optical signal to the tissue stored in the storage 290 at the third location ③ on the circumference of the storage 290.

The optical signal receiver 422 receives an optical signal including an index of refraction at the tissue 1 and an intensity of light at the third position ③ on the circumference of the storage 290.

The received optical signal may be transmitted to the controller 500.

The controller 500 may compare the received optical signal with a level of a preset reference optical signal, and inspect and determine a biopsy of the lesional tissue 1 in real time.

In addition, the controller 500 may visually display an electric signal and optical signal inspection result using a display 510.

FIG. 5b is a view of the insertable probe for diagnosis of lesional tissue in real time, which includes a medicine introduction line.

Referring to FIG. 5b, a reverse-flow prevention valve V is disposed on the tissue moving line 150. The reverse-flow prevention valve V may be a device such as a check valve.

In addition, a medicine introduction line 160 may be connected to the tissue moving line 150.

The medicine introduction line 160 may receive a medicine for separating the tissue into individual cells from the outside, and supply the medicine to the tissue moving line 150.

Thus, the lesional tissue 1 may be separated into individual cells due to the medicine in the course of introducing the lesional tissue 1 into the guide needle 100 by the compulsory suction force of the pneumatic pump 330 and moving the lesional tissue 1 to the tissue moving line 150.

The tissue separated into individual cells may be moved to and stored in the storage 290.

The tissue 1 stored in the storage 290 undergoes electrical and optical inspection by the inspection unit 400 described with reference to FIG. 5a. Since this process is substantially the same as described above, a repeated description thereof will be omitted.

The pneumatic line 310 extends from the storage 290 by a predetermined length and includes a branch line 320 connected to the pneumatic pump 330.

Thus, the tissue 1 after inspection is discharged to the outside along the pneumatic line 310 by the compulsory suction force of the pneumatic pump 330.

FIG. 6a is a view of the insertable probe for diagnosis of lesional tissue in real time according to the present invention, which employs another inspection unit.

Referring to FIG. 6a, the first and second locations and of the inspection unit 400 may be set at locations on the circumference of the storage 290 facing each other, and the third and fourth locations and may also be set at location on the circumference of the storage 290 facing each other.

In this case, optical fibers 420a of the electric signal lines 410a may be disposed in parallel.

FIG. 6b shows an insertable probe for diagnosis of lesional tissue in real time according to the present invention, which employs another inspection unit.

Referring to FIG. 6b, the first and second locations and of the inspection unit 400 may be set at locations on the circumference of the storage 290 facing each other, and the third and fourth locations and may be set at location on the circumference of the storage 290 facing each other.

Here, the electric signal lines 410a follow the same line upwards and downwards, and the optical fibers 420a follow the same line upwards and downwards.

The electric signal lines 410a and the optical lines 420a are disposed in parallel.

FIG. 7a is a sectional view of an insertable probe for diagnosis of lesional tissue in real time according to another embodiment of the invention, FIG. 7b is a sectional view taken along line a-a' of FIG. 7a, and FIG. 7c is a view of an insertable probe for diagnosis of lesional tissue in real time according to a further embodiment of the invention.

Other embodiments of the probe according to the present invention will be described with reference to FIGS. 7a to 7c.

Referring to FIGS. 7a and 7b, a guide needle 100 (see FIG. 6b) is formed of a metal and a region of the guide needle 100 to be inserted into the human body except for one end of the guide needle 100 may be coated with an insulating material.

An anti-clogging needle 130 having an outer diameter smaller than an inner diameter of the guide needle 100 is disposed in the guide needle 100.

Here, the anti-clogging needle 130 includes a plurality of different electrodes 140. Of course, the guide needle 100 may also include an electrode.

The anti-clogging needle 130 includes a needle body 131 and an insulating material 132 coated on an outer circumference thereof.

The electrodes 140 are disposed on a surface of the needle body 131 to be exposed outside.

Thus, the insulating material 132 is not coated at a portion on which the electrode 140 is disposed. Instead, the insulating material 132 is formed in a cut shape at the portion on which the electrode 140 is disposed.

Thus, the electrodes 140 may have a predetermined minimum linewidth, and may acquire an electric signal regarding the tissue in the human body.

In addition, the electrodes 140 may be formed at the same height from a surface of the guide needle 100 or the needle body 131 of the anti-clogging needle 130 or, may be formed at different heights from the surface thereof.

The electrodes 140 are separated from each other.

As shown in FIG. 7c, entire surfaces of the electrodes 140 may be coated with an insulating material 132'.

In this state, an electric signal is applied to the electrodes 140 and is measured simultaneously or individually, and an electric signal on tissue in the human body can be acquired.

FIG. 8a is a view of an insertable probe for diagnosis of lesional tissue in real time according to yet another embodiment, FIG. 8b is a sectional view taken along line b-b' of FIG. 8a, and FIG. 8c is a view of an insertable probe for diagnosis of lesional tissue in real time according to yet another embodiment.

Referring to FIGS. 8a and 8b, a guide needle 100 (see FIG. 6b), an inner cylinder, or a needle body 131 of an anti-clogging needle 130 is provided with a plurality of different electrodes 141, each of which has a predetermined minimum linewidth to acquire an electric signal of tissue in the human body.

Here, as shown in FIGS. 8b and 8c, a portion or the entirety of the surfaces of the electrodes 141 may be coated with insulating materials 133, 133'.

In the former case, each of the electrodes 141 is stepped to be partially exposed outside. The remaining area of the electrode 141 is coated with an insulating material 133.

Thus, application of an electric signal to the electrodes 141 and measurement of the electric signal are simultaneously or individually performed, and an electric signal regarding tissue in the human body can be acquired.

Next, various embodiments of the tissue collection portion according to the invention will be described.

FIG. 9a is a sectional view of another embodiment of the tissue collection portion according to the present invention, and FIG. 9b is a longitudinal sectional view of another embodiment of the tissue collection portion according to the present invention.

Referring to FIGS. 9a and 9b, the probe according to the present invention includes a hollow outer needle 610, an inner needle 620 inserted into a hollow portion of the outer needle 610 to be horizontally moved in a longitudinal direction of the outer needle 610 and having a sharp distal end, and a tissue collection portion 700 formed in the inner needle 620 to collect a predetermined amount of tissue.

Here, the tissue collection portion 700 is formed in a recess shape having a predetermined depth on a circumference of the inner needle 620.

Opposite sidewalls of the tissue collection portion 700 are gradually widened from upper ends thereof to lower ends thereof.

FIG. 10a is a sectional view of one example in which an electrode is disposed on a bottom surface of an anti-clogging needle of FIG. 9a, and FIG. 10b is a longitudinal sectional view of the example in which the electrode is disposed on the bottom surface of the anti-clogging needle of FIG. 10a.

Referring to FIGS. 10a and 10b, the probe may include one or a plurality of electrodes 630.

Here, the electrode 630 is disposed on the outer circumference of the inner needle 620.

FIG. 11a is a sectional view of one example in which an electrode is disposed in a tissue collection portion of FIG. 9a.

FIG. 11b is a longitudinal sectional view of the example in which the electrode is disposed in the tissue collection portion of FIG. 9a.

Referring to FIGS. 11a and 11b, an electrode 631 may be disposed in close contact with a surface of the inner needle 620 and a surface of the tissue collection portion 700.

The electrode 631 may be attached to a bottom surface and a sidewall of the tissue collection portion 700 formed in a recess shape and to a surface of the inner needle 620 to form a single body.

Next, a method of manufacturing an electrode according to the present invention will be described with reference to FIGS. 12a to 14c.

Referring to FIGS. 12a to 12i, the method of manufacturing an electrode according to the present invention includes a) depositing a polymer (for example, parylene) P1 and P2 to form a photomask having different electrode patterns, b) securing an anti-clogging needle or an inner cylinder, followed by coating a photoresist 21 onto the anti-clogging needle 50 or the inner cylinder, and c) forming an electrode 1 in a curved structure using the anti-clogging needle 50 or the inner cylinder coated with the photoresist 21.

The depositing a polymer includes depositing a nitride 20 on a silicon substrate 10, forming a pattern of a membrane section 30 of the photomask in the nitride 20, etching the silicon substrate 10 to a predetermined depth in a thickness direction of the silicon substrate 10, depositing first parylene P1 on the nitride 20 and the silicon substrate 10, depositing chromium Cr on the first parylene P1, and forming patterns of different electrodes, depositing second parylene P2 on the chromium Cr, etching the first parylene P1 and the second parylene P2 in the membrane section 30, and etching the silicon substrate 10 such that all of a remaining depth of the silicon substrate 10 is etched, and removing the nitride 20.

Referring to FIGS. 13a to 13c, the securing an anti-clogging needle or an inner cylinder includes depositing the nitride 20 on the silicon substrate 10 and forming a securing mold pattern of the anti-clogging needle 50 or the inner cylinder on the nitride 20, etching the silicon substrate 10 to a predetermined depth in a thickness direction of the silicon substrate 10 to form a securing mold 31 of the anti-clogging needle 50 or the inner cylinder, placing the anti-clogging needle or the inner cylinder in the securing mold 30 to secure the anti-clogging needle or the inner cylinder, and coating the photoresist 21 onto the anti-clogging needle 50 or the inner cylinder.

Referring to FIGS. 14a to 14c, the forming an electrode includes aligning the anti-clogging needle 50 or the inner cylinder secured to the securing mold 31 and the photomask such that the anti-clogging needle 50 or the inner cylinder and the photomask contact each other, projecting UV light to the photoresist 21 through the photomask to form patterns of different electrodes at desired locations of the curved surface of the anti-clogging needle or the inner cylinder, and depositing a metal 1 after the patterns are formed, and removing the photoresist 21 to form the electrode 1.

As such, according to the embodiments of the invention, lesional tissue placed at a predetermined depth of the human body may be collected and the collected lesional tissue may be electrically and optically diagnosed and inspected in real time.

According to the embodiments of the invention, a diameter of the guide needle is set to below 5 mm, whereby destruction of tissue in the human body may be minimized through the guide needle and pain of a patient may be minimized.

According to the embodiments of the invention, since electrical and optical inspection information may be obtained in real time by inserting the guide needle at a portion that is doubted to be lesional tissue of a patient, a time consumed in tissue diagnosis may be shortened and accuracy of diagnosis may be increased.

According to the embodiments of the invention, since inspection information may be monitored and stored in real time, diagnosis by a surgical operator may be assisted, and the inspection information may be compared and analyzed later.

Although some embodiments have been described herein, it will be apparent to those skilled in the art that these embodiments are given by way of illustration only, and that various modifications, changes, and alterations can be devised without departing from the spirit and scope of the invention. The scope of the invention should be limited only by the accompanying claims and equivalents thereof.

What is claimed is:

1. An insertable probe for diagnosis of lesional tissue in real time, the insertable probe comprising:
    a guide needle inserted into the human body and having a hollow shape of a predetermined length;
    a storage connected to the guide needle;
    a tissue collection portion configured to collect a predetermined amount of tissue in the human body and move the collected tissue to the storage through the guide needle;
    an inspection unit configured to inspect the tissue stored in the storage;
    an optical fiber having a first end, a second end, and a first length in a longitudinal direction extending from the first end to the second end;
    a plurality of electrodes, the electrodes of the plurality of electrodes comprising a first electrode on a surface of the optical fiber, and a second electrode over the first electrode in a radial direction of the optical fiber;
    wherein a first insulation layer over the first electrode in the radial direction of the optical fiber, wherein the first insulation layer is between the first electrode and the second electrode; and
    a second insulation layer over the second electrode in the radial direction of the optical fiber, wherein the second electrode is between the second insulation layer and the first insulation layer,
    wherein
        the first electrode has a second length in the longitudinal direction less than the first length,
        the second electrode has a third length in the longitudinal direction less than the second length,
        the first electrode is between the second electrode and the surface of the optical fiber,
        the first insulation layer has a fourth length in the longitudinal direction less than the second length and greater than the third length,
        the second insulation layer has a fifth length in the longitudinal direction less than the third length, and
        the first electrode, the first insulation layer, the second electrode, and the second insulation layer are arranged in a sequentially raised stepped structure over the surface of the optical fiber in the radial direction of the optical fiber.

2. The insertable probe according to claim 1, wherein the guide needle is formed of a metal, a region of the guide needle to be inserted into the human body except for one end of the guide needle is coated with an insulating material, an anti-clogging needle having an outer diameter smaller than an inner diameter of the guide needle is disposed within the guide needle, and the one end of the guide needle and the anti-clogging needle are different electrodes to acquire an electric signal regarding the tissue.

3. The insertable probe according to claim 1, wherein the guide needle is formed of a metal, a region of the guide needle to be inserted into the human body except for one end of the guide needle is coated with an insulating material, an anti-clogging needle having an outer diameter smaller than an inner diameter of the guide needle is disposed within the guide needle.

4. The insertable probe according to claim 1, wherein an inner cylinder having an outer diameter smaller than an inner diameter of the guide needle is disposed within the guide needle and comprises the optical fiber to acquire an optical signal regarding the tissue.

5. The insertable probe according to claim 1, wherein the first and second electrodes are separated from each other by an insulating layer.

6. The insertable probe according to claim 1, wherein the tissue collection portion comprises:
    a tissue moving line connecting an interior space of the guide needle to the storage;
    a wire disposed within the guide needle and the tissue moving line and provided at one end thereof with a tissue collecting member to collect a predetermined amount of tissue in the human body; and
    a drive unit connected to an opposite end of the wire to pull or release the wire such that the tissue in the human body is placed in the storage.

7. The insertable probe according to claim 1, wherein the tissue collection portion comprises:
    a tissue moving line connecting an interior space of the guide needle to the storage; and
    a pneumatic pump connected to the storage and suctioning the tissue in the human body through the tissue moving line to store the suctioned tissue in the storage.

8. The insertable probe according to claim 1, further comprising: an actuator, the actuator changing a cross-section of a channel securing the tissue stored in the storage using a predetermined pneumatic pressure.

9. The insertable probe according to claim 7, wherein a medicine introduction line through which a predetermined amount of medicine for disrupting the tissue into individual cells is further connected to the tissue moving line.

10. The insertable probe according to claim 9, wherein the medicine introduction line on the tissue moving line is provided at a front end thereof with a reverse-flow prevention valve to prevent reverse flow of the tissue stored in the storage.

11. The insertable probe according to claim 1, wherein the first electrode, the first insulation layer, the second electrode and the second insulation layer are arranged in the stepped structure over the optical fiber such that a portion of a surface of the first electrode opposing the optical fiber is free from being covered by the first insulation layer, a portion of a surface of the first insulation layer opposing the optical fiber is free from being covered by the second electrode, and a portion of a surface of the second electrode opposing the optical fiber is free from being covered by the second insulation layer.

12. The insertable probe according to claim 1, wherein a portion of the first electrode having a length equal to a difference between the second length and the fourth length is free from being covered by the first insulation layer, a portion of the second electrode having a length equal to a difference between the third length and the fifth length is free from being covered by the second insulation layer.

* * * * *